United States Patent [19]
Jimenez et al.

[11] Patent Number: 5,888,551
[45] Date of Patent: Mar. 30, 1999

[54] HAIR GROWTH STIMULATING COMPOSITION

[75] Inventors: Joaquin Jimenez, Miami; Adel A. Yunis, Boca Raton, both of Fla.

[73] Assignee: University of Miami, Miami, Fla.

[21] Appl. No.: 570,411

[22] Filed: Dec. 11, 1995

[51] Int. Cl.⁶ .................................................. A61K 35/14
[52] U.S. Cl. ............................................................. 424/534
[58] Field of Search ................................ 424/520, 195.1, 424/534, 573

[56] References Cited

U.S. PATENT DOCUMENTS 5,093,479  3/1992  Fabricius et al. ...................... 530/351

FOREIGN PATENT DOCUMENTS 492614  7/1992  European Pat. Off. .
93/04164  3/1993  WIPO .

OTHER PUBLICATIONS

Philpott et al., Journal of Investigative Dermatology 102: 857–861 (1994).
Ohmura et al., Cancer Research 50(1):103–107 (1990).
Bates et al., Immunology 72: 448–450 (1991).
Nakayama et al., Clinical and Experimental Immunology 51: 511–516 (1983).
Low et al., In Vitro Cell Developmental Biology 27A(8):639–645 (1991). Abstract.

*Primary Examiner*—Jean C. Witz
*Attorney, Agent, or Firm*—Morgan & Finnegan, LLP

[57] ABSTRACT

The present invention relates to compositions useful in the stimulation of hair growth. These compositions comprise a conditioned medium obtained from a cell culture of human mononuclear cells or a conditioned or extracted medium obtained from a cell culture of mammalian normal or transformed cells or cancer cells.

3 Claims, 4 Drawing Sheets

HAIR GROWTH STIMULATING COMPOSITION

FIELD OF THE INVENTION

The present invention relates to factors which are capable of stimulating hair growth in a subject.

BACKGROUND OF THE INVENTION

Physiology of Hair Growth. From early fetal development, and through the entire life of animals including humans, hair follicles (HFs) undergo many cycles of degeneration and regrowth. In human hair growth, during the neonatal period and throughout adolescence, HF on scalp progressively thicken because the follicles gradually enlarge with each new cycle (DeVillez R L: In: Current Concept, A Scope Publication, by the Upjohn Co., Kalamazoo, Mich., 1986; pp. 4–27; Takashima I, Kawagihi I: In: Toda K, et al (eds): Biology and Disease of Hair. Baltimore, Univ. Park Press, 1976; pp. 457–471).

The HP is composed of many cell types, such as epidermal and mesenchymal cells. The mesenchymal cells are known to play a role as "inductive organizers" of both fetal and postnatal follicles (Chase H B. Physiol Rev. 1954; 34:113–126).

The follicular germ cells, which are the bulbar matrix cells, are responsible for the great mitotic proliferation in the HF. During development, the cells in the matrix proliferate with an upward migration and differentiation into hair matrix, inner sheath and outer sheath cells. The hair matrix group, located in the central axis of the HF, further differentiates into the cells forming the medulla, hair cortex, and hair cuticle. These cells show a continuous upward migration with keratinization of the cortical and cuticle cells which are essential for the manufacturing process of hair in a growing follicle (Chase H B. Physiol Rev. 1954; 34:113–126; Hashimoto K. Br J Dermatol 1970; 83:167–176).

Hair cycles are divided into three stages: 1) Anagen, which is the active growing phase of the HF cycle, 2) Catagen, a regressive stage, 3) Telogen, resting stage. (DeVillez R L: In: Current Concept, a Scope Publication by the Upjohn Co., Kalamazoo, Mich., 1986; pp. 4–27.; Takashima I, Kawagishi I: In: Toda K, et al (eds): Biology and Desease of Hair. Baltimore, Univ. Park Press, 1976; pp. 457–471; Chase H B. Physiol Rev. 1954; 34:113–126; Kligman A M. J Invest Dermatol 1959; 33:307–316.) The relative duration of these stages varies with the individuals' age, hormonal factors, nutritional and health status, as well as genetics. Growth factors responsible for the stimulation of hair growth have not yet been elucidated.

Of the 100,000 to 150,000 scalp hairs on a human adult, approximately 90% are in anagen, with the remaining 10% in the telogen phase. Approximately 50 to 100 clubbed hairs are shed each day. The growth rates of human hairs vary slightly depending on the body region, with 0.44 mm/day at the vertex of the scalp then 0.27 mm/day for beard or body hair. (Moretti G, Rampini E, Rebora A: Int J Dermatol 15:277–285, 1976; Orentreich N, Durr N P: Clin Plast Surg 9:197–205, 1982; Katz M, Wheeler K E, Radowsky M. et al. Med biol Eng Comput 17:333–336, 1979.

In animal species such as rats and mice, all hairs are apparently in the same state of activity, where all cyclic changes are synchronized (DeVillez R L: In: Current Concept, A Scope Publication, by the Upjohn Co., Kalamazoo, Mich., 1986; pp. 4–27; Takashima I, Kawagihi I: In: Toda K, et al (eds): Biology and Disease of Hair. Baltimore, Univ. Park Press, 1976; pp. 457–471). The first cycle of hair growth in rats starts early after birth and continues through to approximately the 21st day of life. The second cycle starts approximately after day 35.

The young (8–12days) rat has been previously utilized as a model for chemotherapy-induced alopecia and a number of novel observations have been made (Hussein, A. M., Jimenez, J. J., McCall, C. A., and Yunis, A. A.: Science 249:1564, 1990; Jimenez, J. J., Wong, G. H. W., Yunis. A. A.: FASEB J. 5:2456, 1991; and Jimenez, J. J., Huang, H. S., and Yunis, A. A. Cancer Invest. 10(4):269, 1992; Jimenez, J. J. and Yunis, A. A.: Cancer Res. 52:413, 1992; Jimenez, J. J., Sawaya, M. E. and Yunis, A. A.: FASEB J. 6:911, 1992; Jimenez, J. J. and Yunis A. A.: Cancer Res. 52:5123, 1992; and Jimenez, J. J., Alvarez, E., Bustamante, C. D., and Yunis, A. A. Am. J. of the Med. Sci 310(2):43, 1995. Rats treated with chemotherapy during the first cycle of hair growth become totally alopecic within 10 days. These rats remain with total alopecia until the second cycle of hair growth. Thus it takes 20 to 30 days for rats to recover from the alopecia.

More recently, applicants have used a commercial hair remover, Neet®, on rats during their first cycle of hair growth. This approach makes the rats immediately alopecic, and hair does not regrow until the second cycle. Applicants believe that this long latent period could be used effectively to test various substances for their potential ability to stimulate hair growth and thus shorten the time to recovery.

It is an object of the present invention to determine the possible existence of hair growth-stimulating activity or of hair growth-stimulating factors.

SUMMARY OF THE INVENTION

It has been found that conditioned or extracted medium from mammalian normal, transformed or cancer cells, and preferably from conditioned or extracted medium from human mononuclear cells obtained from buffy coats and conditioned medium from the human pancreatic carcinoma cell line MIA PaCa (Yunis, A. A., Arimura, G. K., and Russin, D. J., Int. J. of Cancer, 19:128, 1977) possess hair growth-stimulating activity. This activity was determined by use of a screening process in which various compounds and/or cytokines were tested.

BRIEF DESCRIPTION OF THE FIGURES

The file of this patent contains at least one drawing executed in color. Copies of this Patent with color drawing (s) will be provided by the patent and Trademark Office upon request and payment of the necessary fee.

DETAILED DESCRIPTION OF THE INVENTION

Figure 1:
FIG. 1 is a photograph of two groups of rats which were all treated with CTX. The top group of rats were treated with a hair growth stimulating composition according to the present invention and the bottom group were treated with control medium.

The present invention relates, in general, to compositions for stimulating hair growth and methods for stimulating hair growth. Hair growth stimulation may be desirable, for example, in alopecia conditions induced by chemotherapeutic treatment or in post hair graft treatment. Additionally, hair growth stimulation may be a goal in simply enhancing normal hair growth in a subject or in alleviating the effects of thinning hair.

It should be noted that by stimulation of hair growth as used herein applicants intend to encompass the stimulation of the growth of existing hair or the stimulation of hair growth from the hair follicle.

Hair growth stimulation is a commonly sought goal in various situations. Alopecia is a common and distressing side effect of various chemotherapeutic agent. There is an urgent need in such situations to enhance the growth of hair to restore the original state of a subject suffering from such alopecia. Similarly, hair growth stimulation is a requirement after hair graft procedures so that the grafted hairs may quickly grow and provide a fuller hair condition than may have been present prior to the hair graft procedure. Some normal subjects may also desire to have a fuller hair condition and, hence, a hair growth stimulating composition would also be desirable for such subjects.

Compositions suitable for use in the present invention comprise formulations containing the active materials in accordance with the present invention either by themselves or in association with a pharmaceutically acceptable vehicle therefore and optionally other therapeutic ingredient(s). The vehicle (Hashioto K. Br J. Dermatol 1970; 83:167–176) must be "acceptable" in the sense of being compatible with the other ingredients of the preparation and not deleterious to the recipient thereof.

The instant active materials are normally administered in topical form such as a liniment, a lotion, a cream or a gel. Additionally, the instant active materials may be administered intracutaneously (intradermally). Further therapeutic ingredients which might be present include, for example, vitamin $D_3$ and its analogs, derivatives or active metabolites or a potassium channel opener such as minoxidil, cromokalin or pinacidil. The concentration of the active ingredients will generally be between about 1 and 100 $\mu g/g$. The instant formulations can be applied from once to several times daily for prolonged periods of time if such is required.

Preparations suitable for topical administration include liquid or semi-liquid preparations such as liniments, lotions, applicants, oil-in-water or water-in-oil emulsions as creams, ointments, pastes or gels, or solutions or suspensions. Intracutaneous preparations contain the present active material and the known generally accepted intracutaneous excipients, carriers and additives.

In addition to the aforementioned ingredients, the preparations of this invention may include one or more additional ingredients such as diluents, buffers, flavoring agents, binders, surface active agents, thickeners, lubricants, preservatives, e.g. methyl hydroxybenzoate (including anti-oxidants), emulsifying agents and the like.

The preparations may as mentioned above, contain further therapeutically active compounds usually applied in the above mentioned treatment.

In the topical treatment, ointments, creams, gels, or lotions containing from 1–100 $\mu g/g$ of the instant active principles are administered.

The present invention further concerns a method for treating subjects suffering from or in risk of getting alopecia, said method consisting of administering topically to a subject in need of treatment to stimulate hair growth an effective amount of instant active materials, alone or in combination with one or more other therapeutically active compounds usually applied in such treatment. The treatment with the present compounds concomitantly with further therapeutically active compounds may be simultaneous or with intervals.

In the instant invention, the existence of a heretofore unknown hair growth-stimulating activity or factors have been found. The hair growth-stimulating activity or factors are produced by mammalian normal or transformed cells including, for example normal or transformed human cells as well as some tumor cells or cell lines. The hair growth-stimulating compositions comprise condition media obtained from cultures such cells and preferably of human mononuclear cells or a human pancreatic cancer cells.

A screening process was conducted in which a number of compositions and/or cytokines were tested. For the purpose of testing two models were used:

1. Rats which have been rendered alopecic by chemotherapy (Cytoxan).

2. Rats rendered alopecic by depilation using the hair remover Neet®.

From the screening process, it was unexpectedly discovered that conditioned medium from human mononuclear cells (obtained from buffy coats) and conditioned medium from the human pancreatic carcinoma cell line MIA PaCa (Yunis, A. A., Arimura, G. K., and Russin, D. J., Int. J. of Cancer, 19:128, 1977) contained hair growth-stimulating activity (HGSA).

In rats rendered alopecic with either Cytoxan (CTX) or Neet®, treatment with Human Mononuclear Cell Conditioned Medium, HKCC, resulted in more rapid recovery of hair regrowth than controls, i.e. HKCC contains hair growth-stimulating activity or factor. Thus, it can be concluded that human mononuclear cells produce hair growth-stimulating activity or factor.

In rats rendered alopecic with Neet® (Cytoxan model not used), treatment with Human Pancreatic Cancer Cell Conditioned Medium, MPCM, also resulted in more rapid regrowth of hair than in controls. Thus, certain cancer cells can also produce hair growth-stimulating activity or factor.

Although the foregoing invention has been described in some detail by way of illustration and example for purposes of clarity of understanding, it will be obvious to those skilled in the art that certain changes and modifications may be practiced without departing from the spirit and scope thereof as described in the specification and as defined in the appended claims.

EXPERIMENTAL PROCEDURES

Sprague Dawley rats were used. Rats were fed and housed according to NIH guidelines. Cyclophosphamide or Cytoxan (CTX) was from Adria Laboratories (Columbus, Ohio). CTX (35 mg/kg) was given for one day only on day 11.

PREPERATION OF CONDITIONED MEDIUM FROM HUMAN MONONUCLEAR CELL PREPARATIONS

Buffy coats were purchased from the American Red Cross (Miami, Fla.). The buffy coats were diluted 1:4 with Dulbecco's Modified Eagle's Media, DMEM, (GIBCO) with 10% fetal calf serum (Media Facility Cancer Center, Miami, Fla.). The cell suspension was placed on a gradient (Histopaque-1077, Sigma Diagnostics) and centrifuged for 40 minutes at 1400 rpm. The interface was collected, diluted 1:5 with 10% fetal calf serum (FCS) and centrifuged for 10 minutes at 800 rpm. This procedure was repeated to wash the mononuclear cells.

The cells were resuspended in DMEN with 1% FCS, counted and assessed for morphology. This procedure yielded on an average 35% monocytes and 65% lymphocytes. The cells were then plated at $3\times10^6$/ml in DMEN with 1% FCS in tissue culture dishes (Sarsteadt) and incubated for 24 hr in a humidified incubator at 37° with 5% $CO_2$. At the end of the incubation period, the supernatant was collected and centrifuged at 1000 rpm at 5° for 10 minutes.

The conditioned medium, containing the hair growth stimulating activity (human mononuclear cell conditioned medium or HMCCN), was collected and filtered with $0.2\mu$ filter. Samples were aliquoted and those not used immediately were stored at −70°.

PREPERATION OF MIA PaCa CONDITIONED MEDIUM

MIA PaCa cells were grown to confluence in DMEM with 10% FCS and 2.5% horse serum (HS). Plates were washed ×2 and fresh media was added. The cells were then incubated for 24 hr. in a humidified incubator at 37° with 5% $CO_2$. At the end of the incubation period, the supernatant was collected and centrifuged at 1000 rpm at 5° for 10 minutes. The conditioned media (MIA PaCa conditioned medium or MPCM), containing the hair growth stimulating activity, was collected and filtered with $0.2\mu$ filter. Samples were aliquoted and those not used immediately were stored at −70°.

Control medium was prepared similarly but without cells. Serum Free MPCM (S.F. MPCM) was prepared as follows: MIA PaCa cells were grown to confluence in DMEM with 10% FCS and 2.5% H.S. Plates were washed ×2 with S.F. media and fresh S.F. media was added. After 48 hr. of incubation, the supernatant was collected, centrifuged at 1000 rpm at 5° C. for 10 minutes, filtered with $0.2\mu$ filter and used for ultrafiltration.

CONCENTRATION OF MPCM

This was accomplished by ultrafiltration at 5° C. The MPCM was ultrafiltered in 400 ml batches through a filter with molecular weight (MW) cut off of 10 Kd at an operating pressure of 25 p.s.i. The 2-fold concentrated MPCM was collected and the effluent discarded. The S.F. MPCM was similarly concentrated 10 fold. For control rats, serum free DMEM was similarly concentrated 10 fold. Samples were aliquoted and frozen at −70° until used.

EXAMPLE I

Six 11-day old rats were given CTX 35 mg/kg i.p. Ten days later, when the rats were totally alopecic, they were randomized in two groups of 3 rats each. Group #1 received 0.3 ml of HMCCM s.c. on the head area daily for 10 days. Group #2 received 0.3 ml of control media s.c. on the head area daily for 10 days and served as control. Rats in group #1 demonstrated increased hair growth five days earlier than rats in group #2. Picture was taken on day 35. (FIG. 1).

EXAMPLE II

Figure 2A:
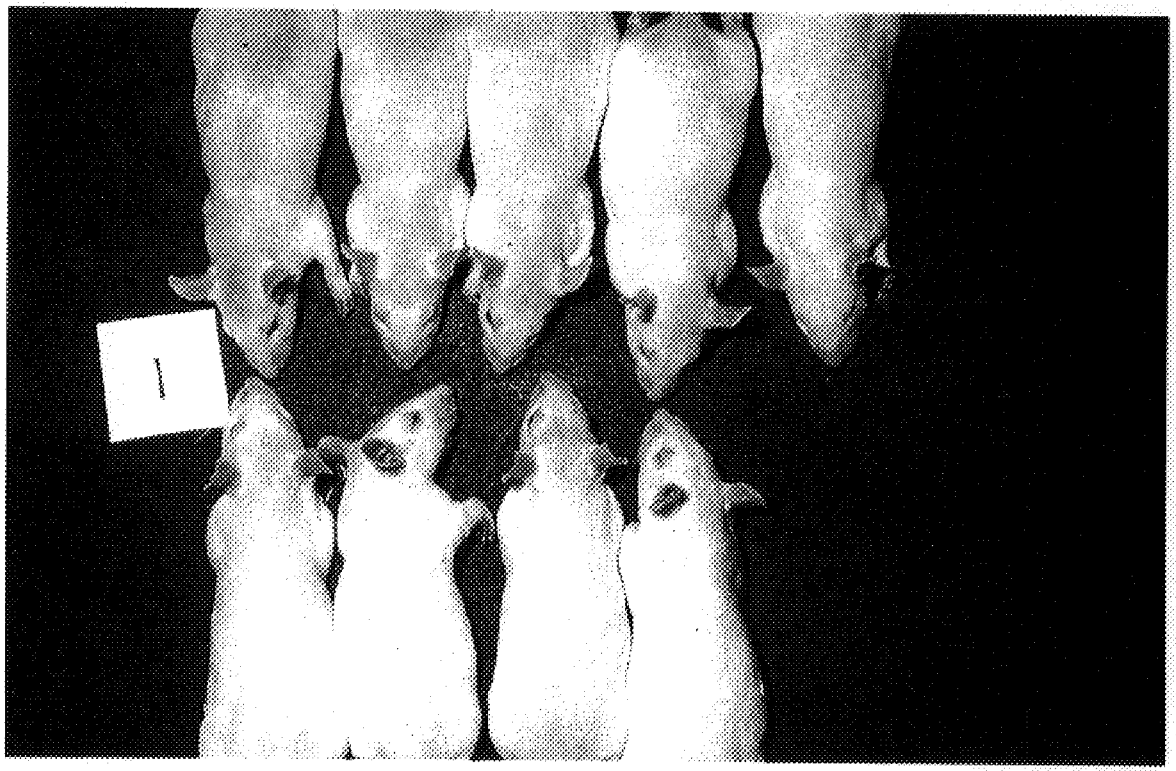
FIG. 2a is a photograph of a group of rats who were treated with CTX and then with a hair growth stimulating composition according to the present invention.
Figure 2B:
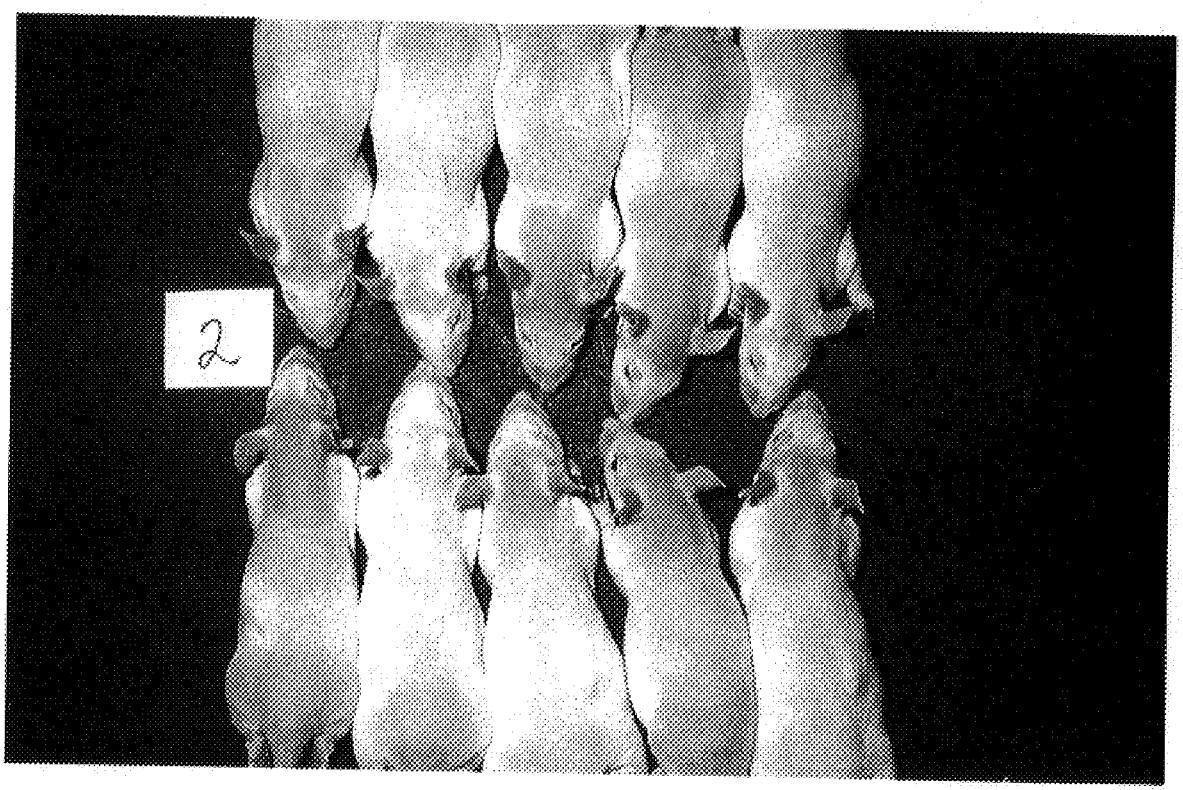
FIG. 2b shows a second group of rats treated with CTX and then with control medium.

Nineteen 11-day old rats were given CTX 35 mg/kg i.p. Ten days later, when the rats were totally alopecic, they were randomized in two groups of 9 and 10 rats respectively. Group #1 (9 rats) received 0.3 ml of HMCCM s.c. on the back area daily for 10 days. Group #2 (10 rats) received 0.3 ml of control media s.c. on the back area daily for 10 days and served as control. Rats in group #1 demonstrated increased hair growth five to six days earlier than rats in group #2 (Picture was taken on day 35). (FIGS. 2a and 2b).

EXAMPLE III

Using Neet®, all hair was removed from nine 26-day old rats. Three groups of 3 rats were randomly selected. Group #1 received 0.5 ml of HMCCM s.c. on the back area daily for 6 days. Group #2 received 0.5 ml of MPCM similarly. Group #3 received control media. Six days after the first injection, three independent observers, not involved in the experiments, were asked to select the rats with increased hair growth.

| HAIR GROWTH STIMULATION | | | |
|---|---|---|---|
| | HMCCM Group #1 | MPCM Group #2 | Control M Group #3 |
| Observer #1 | + | + | − |
| Observer #2 | + | + | − |
| Observer #3 | + | + | − |

EXAMPLE IV

Figure 3:
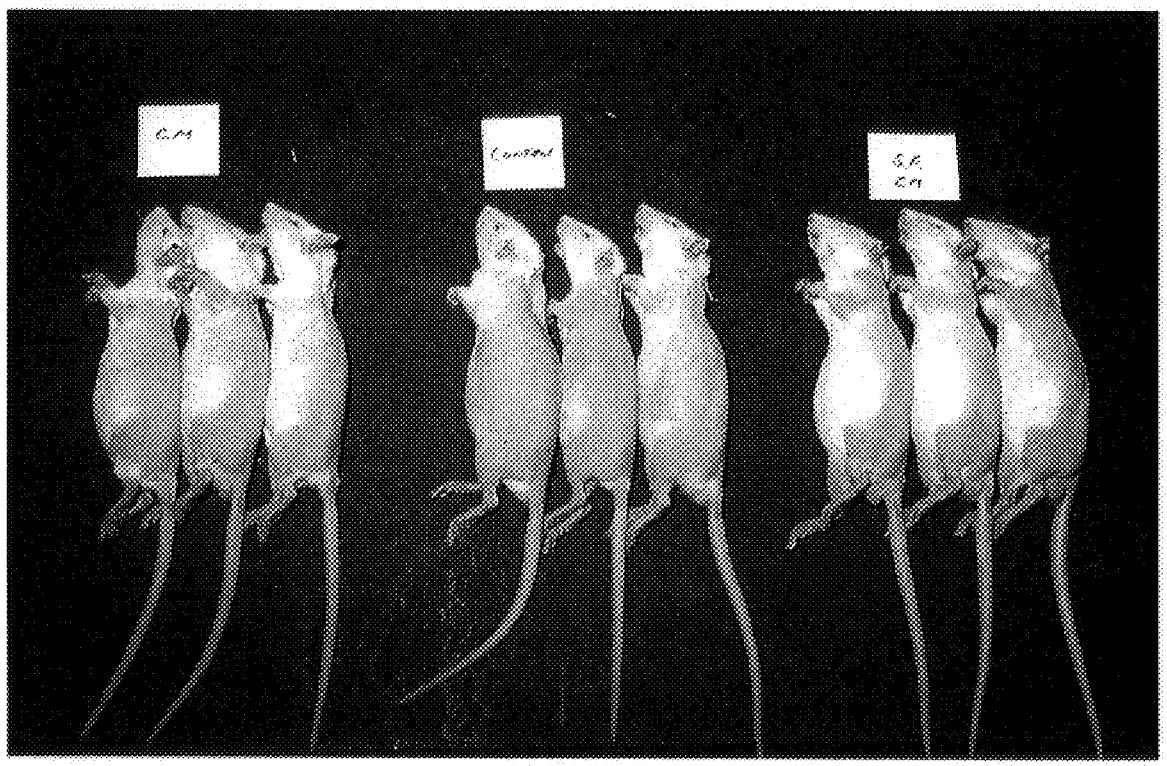
FIG. 3 shows a group of rats treated with CTX. The right hand and left hand groups were treated with compositions according to the invention while the center group were treated with control medium.

Using Neet®, all hair was removed from nine 23-day old rats. Three groups of 3 rats were randomly selected. Group #1 received 0.5 ml of 10× S.F. MPCM on the back area daily for 7 days. Group #2 received 0.5 ml of 2× MPCM (containing serum). Group #3 received 10× control S.F. media and served as control. Seven days after the first injection pictures were taken (FIG. 3). The pictures clearly demonstrate that rats which received 10× S.F. MPCM or 2× MPCM had increased hair regrowth.

We claim:

1. A method of stimulating hair growth in a subject comprising treating said subject with an effective amount of a composition comprising a conditioned medium obtained from a cell culture of human mononuclear cells wherein said medium contains hair-growth stimulating activity or factors.

2. The method of claim 1, wherein the treatment of said subject is a topical or intracutaneous treatment.

3. The method of claim 1, wherein cells are plated in tissue culture dishes and incubated and supernatant from the cell culture comprising the conditioned medium is collected and filtered.

* * * * *